United States Patent
Moroney, III et al.

(10) Patent No.: US 8,308,641 B2
(45) Date of Patent: Nov. 13, 2012

(54) BIOMETRIC MONITOR WITH ELECTRONICS DISPOSED ON OR IN A NECK COLLAR

(75) Inventors: Richard M. Moroney, III, Princeton, NJ (US); Larry Nielsen, Burlington, MA (US); Suzanne M. Kavanagh, Andover, MA (US); Ronaldus M. Aarts, Geldrop (NL); Margreet De Kok, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1112 days.

(21) Appl. No.: 12/279,999

(22) PCT Filed: Feb. 6, 2007

(86) PCT No.: PCT/US2007/061639
§ 371 (c)(1),
(2), (4) Date: Aug. 20, 2008

(87) PCT Pub. No.: WO2007/100959
PCT Pub. Date: Sep. 7, 2007

(65) Prior Publication Data
US 2010/0179389 A1 Jul. 15, 2010

Related U.S. Application Data

(60) Provisional application No. 60/777,503, filed on Feb. 28, 2006.

(51) Int. Cl.
*A61B 5/00* (2006.01)
(52) U.S. Cl. ......... 600/301; 600/300; 600/323; 600/324
(58) Field of Classification Search ........................ None
See application file for complete search history.

(56) References Cited

U.S. PATENT DOCUMENTS 4,662,378 A    5/1987  Thomis
(Continued)

FOREIGN PATENT DOCUMENTS

EP    1671578 A1    6/2006
(Continued)

OTHER PUBLICATIONS

Asada, H. H., et al.; Mobile Monitoring with Wearable Photoplethysmographic Biosensors; 2003; IEEE Engineering in Medicine and Biology Magazine; pp. 28-40.
(Continued)

*Primary Examiner* — Gregory A Morse
*Assistant Examiner* — Bobby Soriano

(57) ABSTRACT

A highly portable biometric monitor is disclosed. At least one remote sensor member (12, 12') includes one or more biometric sensors (20, 22, 24, 25) configured for operative coupling with a patient. A neck collar (14, 114, 214, 314, 414) includes electronics (36, 40, 42, 44, 46, 48) for operating the at least one remote sensor member. The at least one remote sensor member is separate from and not disposed on the neck collar. Optionally, the collar also includes one or more biometric sensors (53). A communication link (18) operatively connects the remote sensor member and the electronics of the neck collar. A motion sensor (26) and position sensor (28) may be disposed with the one or more biometric sensors to sense movement and position, and the electronics (36, 40, 42, 44, 46, 48) configured to account for error in a signal produced by the one or more biometric sensors due to movement sensed by the motion sensor or position sensed by the position sensor. The electronics (36, 40, 42, 44, 46, 48) may log patient activity and body position.

18 Claims, 6 Drawing Sheets

U.S. PATENT DOCUMENTS

| | | | |
|---|---|---|---|
| 4,715,367 A * | 12/1987 | Crossley | 600/27 |
| 5,213,099 A * | 5/1993 | Tripp, Jr. | 600/324 |
| 5,509,421 A * | 4/1996 | Muller et al. | 600/437 |
| 6,160,478 A * | 12/2000 | Jacobsen et al. | 340/539.12 |
| 6,491,647 B1 * | 12/2002 | Bridger et al. | 600/585 |
| 6,594,370 B1 | 7/2003 | Anderson | |
| 6,685,634 B1 * | 2/2004 | Fry | 600/300 |
| 6,796,937 B1 * | 9/2004 | Bates | 600/15 |
| 6,834,436 B2 * | 12/2004 | Townsend et al. | 33/512 |
| 6,997,882 B1 * | 2/2006 | Parker et al. | 600/534 |
| 7,153,262 B2 * | 12/2006 | Stivoric et al. | 600/300 |
| 7,257,438 B2 * | 8/2007 | Kinast | 600/509 |
| 7,301,451 B2 * | 11/2007 | Hastings | 340/539.12 |
| 7,326,179 B1 * | 2/2008 | Cienfuegos | 600/300 |
| 7,559,902 B2 * | 7/2009 | Ting et al. | 600/529 |
| 7,598,878 B2 * | 10/2009 | Goldreich | 340/573.1 |
| 2002/0032386 A1 * | 3/2002 | Sackner et al. | 600/536 |
| 2002/0138027 A1 * | 9/2002 | Bugarin | 602/6 |
| 2003/0065253 A1 * | 4/2003 | Stivoric et al. | 600/300 |
| 2003/0135127 A1 * | 7/2003 | Sackner et al. | 600/536 |
| 2003/0187341 A1 * | 10/2003 | Sackner et al. | 600/388 |
| 2003/0233051 A1 | 12/2003 | Verjus et al. | |
| 2004/0039254 A1 * | 2/2004 | Stivoric et al. | 600/300 |
| 2004/0054291 A1 * | 3/2004 | Schulz et al. | 600/500 |
| 2004/0122408 A1 * | 6/2004 | Potnis et al. | 604/385.24 |
| 2004/0152957 A1 * | 8/2004 | Stivoric et al. | 600/300 |
| 2005/0038348 A1 * | 2/2005 | Avicola et al. | 600/502 |
| 2005/0059870 A1 * | 3/2005 | Aceti | 600/340 |
| 2005/0096513 A1 * | 5/2005 | Ozguz et al. | 600/301 |
| 2005/0113703 A1 * | 5/2005 | Farringdon et al. | 600/509 |
| 2005/0116820 A1 | 6/2005 | Goldreich | |
| 2005/0131288 A1 * | 6/2005 | Turner et al. | 600/391 |
| 2005/0171410 A1 * | 8/2005 | Hjelt et al. | 600/300 |
| 2005/0197552 A1 * | 9/2005 | Baker, Jr. | 600/324 |
| 2005/0206518 A1 * | 9/2005 | Welch et al. | 340/539.12 |
| 2005/0228234 A1 * | 10/2005 | Yang | 600/300 |
| 2005/0240087 A1 * | 10/2005 | Keenan et al. | 600/301 |
| 2005/0240234 A1 * | 10/2005 | Joo et al. | 607/6 |
| 2006/0005843 A9 * | 1/2006 | Nelson et al. | 128/848 |
| 2006/0009697 A1 * | 1/2006 | Banet et al. | 600/485 |
| 2006/0025663 A1 * | 2/2006 | Talbot et al. | 600/365 |
| 2006/0036183 A1 * | 2/2006 | Sackner et al. | 600/481 |
| 2006/0084879 A1 * | 4/2006 | Nazarian et al. | 600/500 |
| 2006/0089538 A1 * | 4/2006 | Cuddihy et al. | 600/300 |
| 2006/0089541 A1 * | 4/2006 | Braun et al. | 600/300 |
| 2006/0122474 A1 * | 6/2006 | Teller et al. | 600/300 |
| 2006/0129050 A1 * | 6/2006 | Martinson et al. | 600/505 |
| 2006/0211936 A1 * | 9/2006 | Hu et al. | 600/386 |
| 2006/0251334 A1 * | 11/2006 | Oba et al. | 382/275 |
| 2006/0252999 A1 * | 11/2006 | Devaul et al. | 600/300 |
| 2007/0055166 A1 * | 3/2007 | Patil | 600/509 |
| 2007/0293781 A1 * | 12/2007 | Sims et al. | 600/534 |

FOREIGN PATENT DOCUMENTS

| | | |
|---|---|---|
| FR | 2801491 A1 | 6/2001 |
| WO | 9923941 A1 | 5/1999 |
| WO | 0237952 A1 | 5/2002 |
| WO | 2005034742 A1 | 4/2005 |
| WO | 2007004083 A1 | 1/2007 |

OTHER PUBLICATIONS

Wood, L. B., et al.; Active Motion Artifact Reduction for Wearable Sensors Using Laguerre Expansion and Signal Separation; 2005; IEEE Engineering in Medicine and Biology; pp. 3571-3574.

Nonin Medical Advertising Brochure "9500 Onyx Digital Finger Pulse Oximetry" © 2002 Nonin Medical, Inc. P/N 2431-000-05 ; www.nonin.com.

Nonin Medical Advertising Brochure "3100 WristOx Wearable Digital Pulse Oximeter" © 2004 Nonin Medical, Inc. P/N 4287-000-02 ; www.nonin.com.

GMP Wireless Medicine Advertising Brochure"LifeSync Wireless ECG Sys", © 2004-2005 GMP Wireless Medicine, Inc. http://www.wirelessecg.com/about_lifesync/index/html.

Medwave Advertisement "Primo Blood Pressure Monitor", Medwave, Inc. 798-0239 Rev B MDWV22006-10,000 www.medwave.com Feb. 21, 2006.

VivoMetrics Advertisement "Peripherals", © 1999-2004 VivoMetrics, Inc. http://www.vivometrics.com/site/system_peripherals.html Feb. 21, 2006.

IM Systems "PAM-RL Records Leg Activity" http://www.imsystems.net/PAM-RL.html Jan. 21, 2006.

Con-Space "Throat Mics", http://www.con-space.com/Pop-Up%20Windows/Accessories/throatmic.html.

* cited by examiner

BIOMETRIC MONITOR WITH ELECTRONICS DISPOSED ON OR IN A NECK COLLAR

CROSS REFERENCE TO RELATED APPLICATIONS

This application claims the benefit of U.S. provisional application Ser. No. 60/777,503 filed Feb. 28, 2006, which is incorporated herein by reference.

The following relates to the medical monitoring arts. It finds particular application in conjunction with monitoring of vital signs such as heart rate, blood oxygen saturation ($SpO_2$), respiration, core body temperature, and so forth, and will be described with particular reference thereto. However, the following is also applicable to biometric monitoring in general.

Monitoring of vital signs such as heart rate, blood oxygen saturation ($SpO_2$), respiration, core body temperature, and so forth, enables early detection of potentially adverse medical conditions, thus in turn enabling early intervention by medical personnel. Such monitoring is advantageously performed continuously, since any interruption in monitoring presents a time interval during which patient deterioration may occur without warning. In particular, it is advantageous to perform continuous vital signs monitoring when the patient is being moved by medical personnel, or when the patient is ambulatory (walking or moving in a wheelchair or other transport-assisting device), since such activities can stress the patient so as to increase the likelihood of onset of a deleterious medical condition.

Traditionally, continuous monitoring has been performed using biometric sensors attached to the patient. These sensors are typically connected by wires with one or more medical monitoring devices each of which typically include alarm annunciation, a display for viewing physiological waveforms and trends of vital signs data, a digital readout showing current vital signs data, storage for storing vital signs data, and so forth. The medical monitoring devices in turn may be connected with a hospital computer network via additional cabling. The extensive wiring and cabling in such traditional monitoring setups is recognized as having significant disadvantages, including reduced patient mobility, compromised patient comfort, hindered patient access, and increased difficulty in moving the patient for x-rays or other diagnostic tests.

Accordingly, there is interest in substituting wireless links for the wiring and cabling of traditional monitoring setups. Medical monitoring devices are sometimes connected with the hospital network via a wireless local area network (WLAN) connection or other wireless digital communication protocol. Additionally, the biometric sensors may communicate with the medical monitoring devices by a short-range wireless communication protocol such as Bluetooth. These approaches reduce or eliminate wiring and cabling, but introduce other disadvantages. Wireless connections are not visible, and so interruption of a wireless link is not readily apparent to medical personnel. Alarms may be provided to indicate loss of wireless communication—however, it can be difficult and stressful for medical personnel to identify the cause of such an alarm. The short-range wireless communication between the biometric sensor and its associated medical monitoring device is particularly susceptible to interruption, for example if the patient is moved or ambulates away from the medical monitoring device. The invisibility of the wireless link between the biometric sensor and the medical monitoring device increases the likelihood that such an interruption will occur, since it is not readily apparent to the patient or to medical personnel that the medical monitoring device must be moved with the patient.

Another problem with using a short-range wireless link between a biometric sensor and the medical monitoring device is that such wireless communication takes relatively substantial electrical power to operate. Thus, the biometric sensor includes an on-board battery or other electrical power source sufficient to drive a short-range wireless transmitter to communicate with the medical monitoring device. Such an on-board battery or other electrical power source is typically bulky and heavy, making the wearing of the biometric sensor uncomfortable for the patient. This discomfort is particularly acute in the case of an ear sensor member that includes biometric sensors operatively coupling to the exterior of an ear or to an ear canal.

The following contemplates improvements that overcome the aforementioned limitations and others.

According to one aspect, a biometric monitor is disclosed. At least one remote sensor member includes one or more biometric sensors configured for operative coupling with a patient. A neck collar includes electronics for operating with the at least one remote sensor member. The neck collar optionally also includes one or more additional biometric sensors disposed with the neck collar. A communication link operatively connects the at least one remote sensor member and the electronics of the neck collar.

According to another aspect, a biometric monitor is disclosed. A sensor member includes: (i) one or more biometric sensors configured to couple with a patient at a coupling point; and (ii) a motion sensor disposed with the one or more biometric sensors to sense movement and/or patient position at the coupling point. Electronics are configured to account for error in a signal produced by the one or more biometric sensors due to movement or change in patient position sensed by the motion sensor.

According to another aspect, a biometric monitor is disclosed. One or more vital signs sensors are configured for coupling with an ear and sense at least pulse rate via the coupled ear. A light emitter is provided. Control circuitry is provided to control blinking of the light emitter in accordance with the sensed pulse rate.

One advantage resides in increased patient comfort.

Another advantage resides in enhanced patient mobility.

Another advantage resides in improved robustness of biometric monitoring against patient ambulating activities and body positions.

Another advantage resides in improved patient safety through convenient and continuous vital signs monitoring.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 shows a perspective view of a biometric monitor including an ear sensor member configured to couple with a patient's ear, tethered with electronics disposed on and/or in a neck collar that has an adjustable collar size implemented as a post-and-hole adjustment system.

FIG. 2 diagrammatically shows a functional block diagram of the biometric monitor of FIG. 1.

Figure 10:
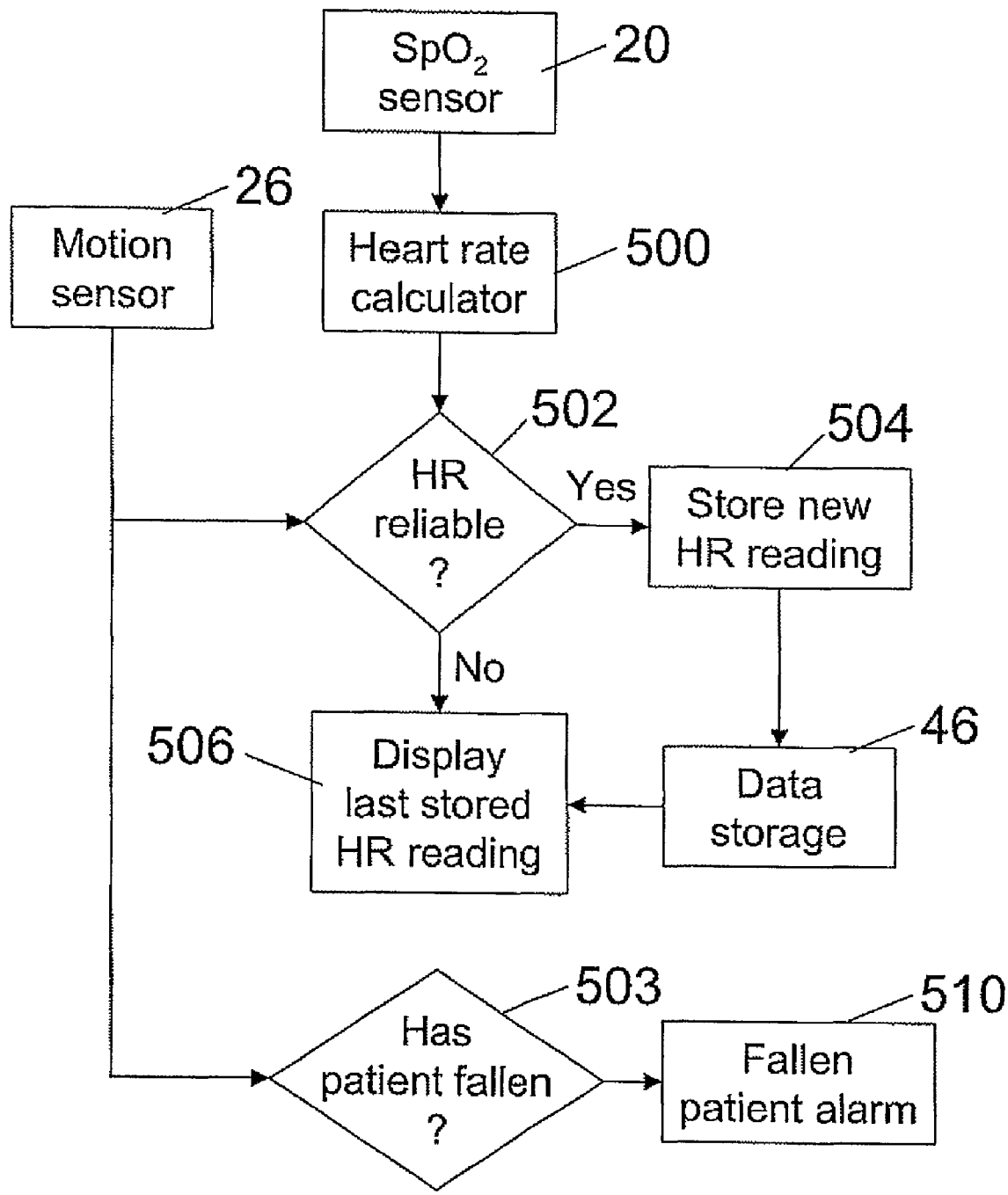

FIG. 10 diagrammatically shows processing performed by the electronics of the neck collar to accommodate head motion monitored by an accelerometer.

Figure 11:
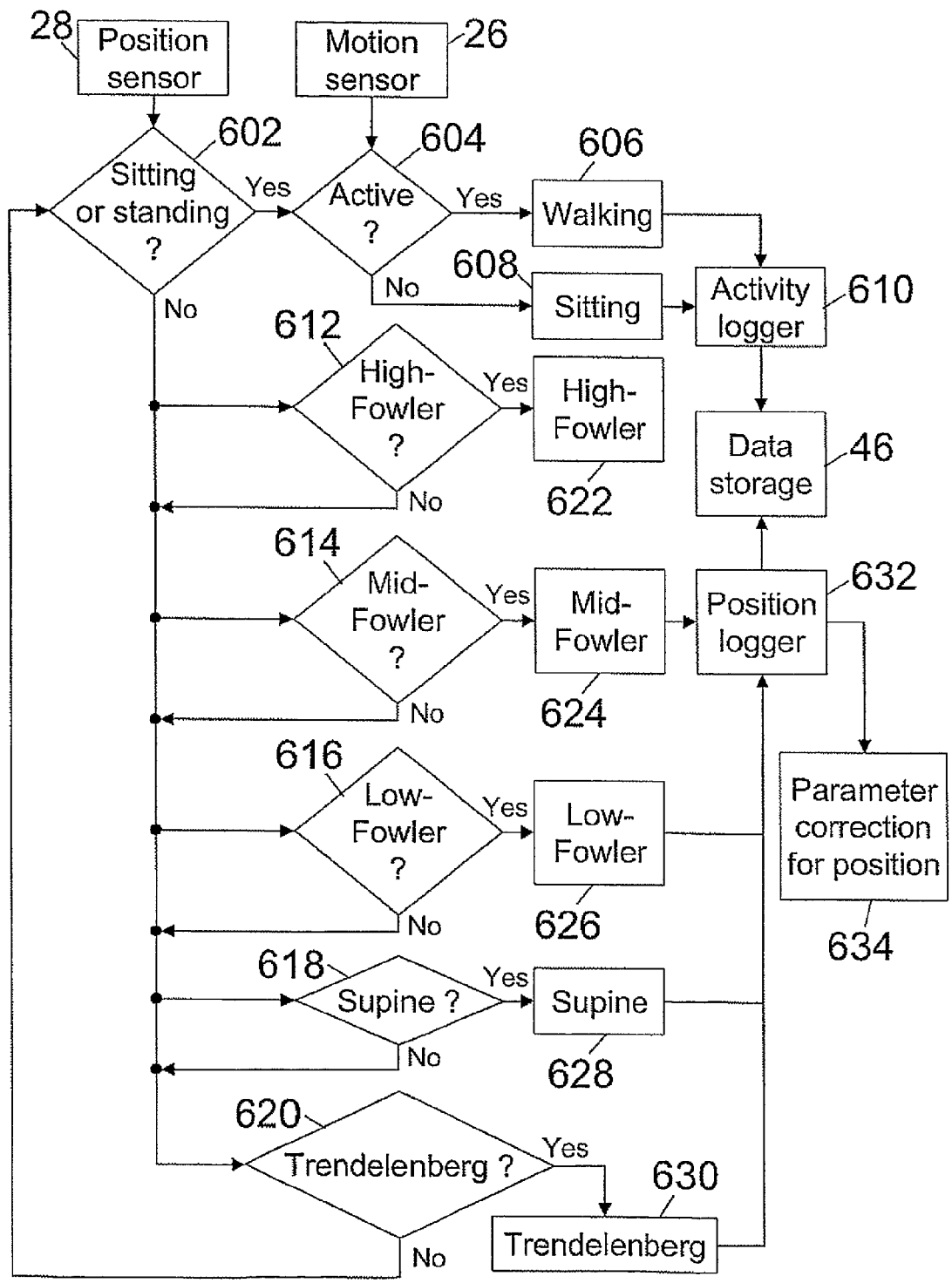

FIG. 11 diagrammatically shows processing performed by the electronics of the neck collar to generate a log of patient activity and body position.

Figure 1:
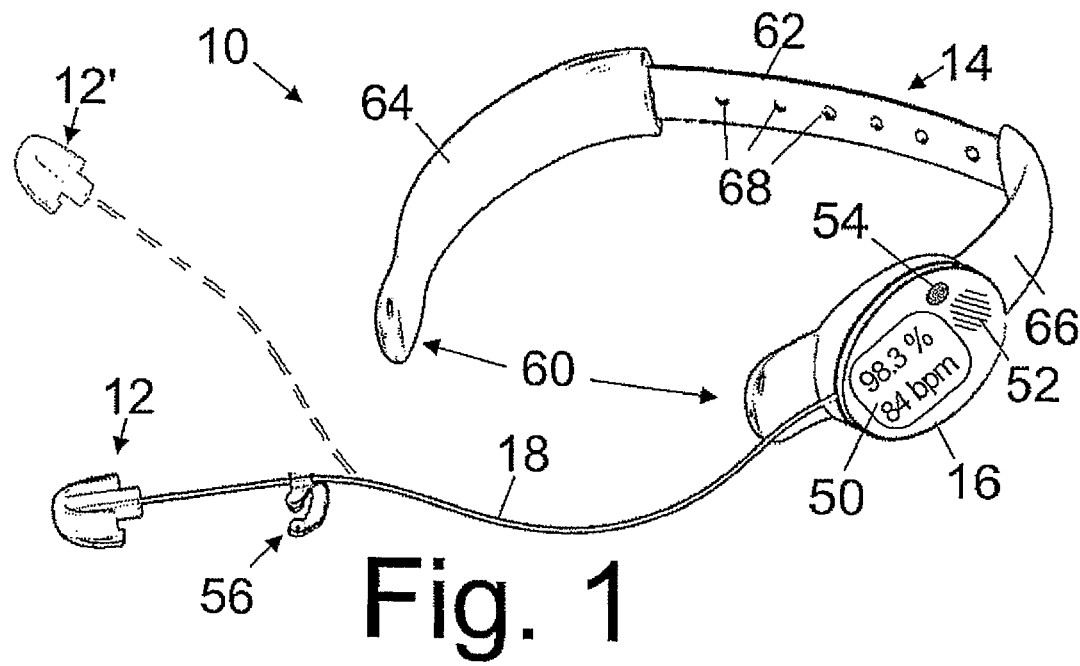
Figure 2:
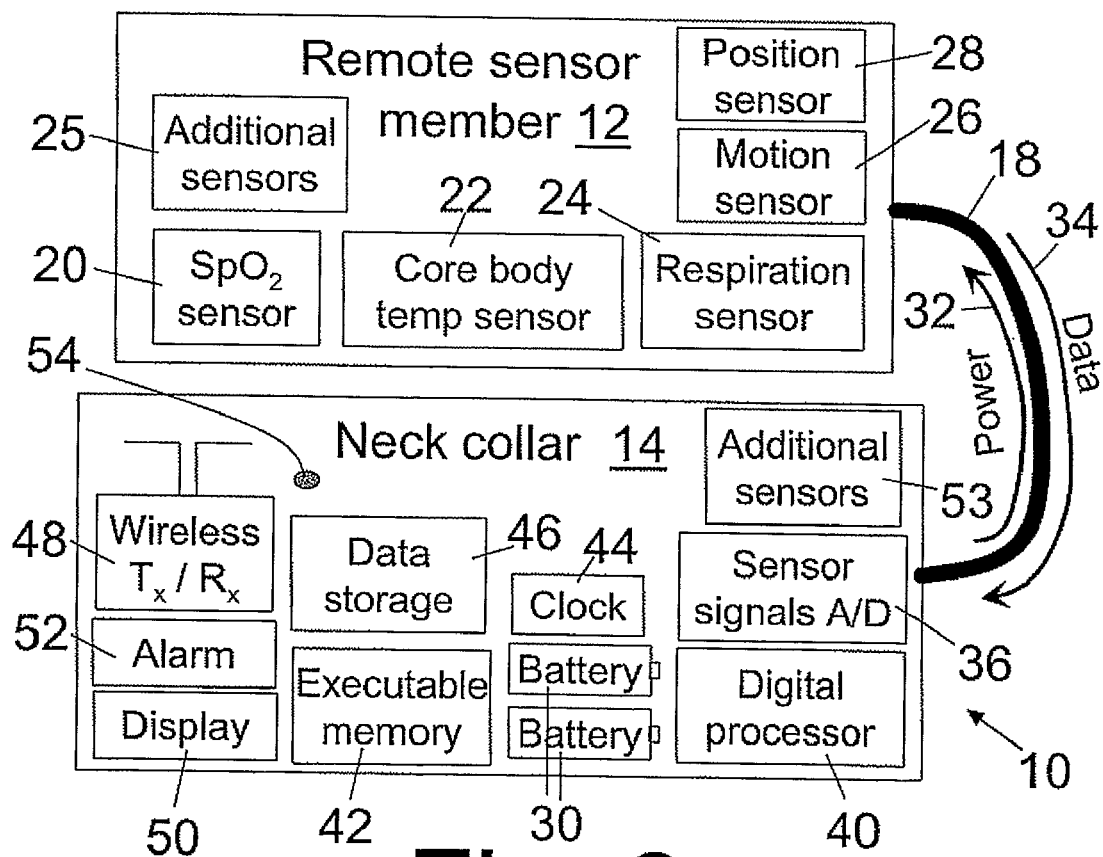

With reference to FIGS. 1 and 2, a biometric monitor 10 includes a remote sensor member 12, which in the illustrated embodiment is configured for coupling with the ear of a patient, and a neck collar 14 configured for disposing around a patient's neck. The neck collar 14 includes an electronics module 16 containing electronics for operating the remote sensor member 12. The remote sensor member 12 is remote in that it is separate from and not disposed on the neck collar 14—in the illustrated embodiments, the remote sensor member 12 is an ear sensor member disposed on or in the ear. In other embodiments, the sensor member may be a finger sensor member disposed on a patient's finger, or may be directly integrated into the electronics module or neck collar, inside the concha of the outer ear, the outer ear or earlobe, the forehead, the nose, the cheek, the tongue, the neck, the wrist, the arm, the belly-button or stomach, the ankle, or so forth. A flexible tether 18 connects the sensor member 12 and the electronics of the neck collar 14. The ear sensor member 12 is a lightweight unit that includes one or more biometric sensors, such as the illustrated example blood oxygen saturation ($SpO_2$) sensor 20, core body temperature sensor 22, and respiration sensor 24. Other or additional biometric sensors 25 are also contemplated for inclusion in the sensor member 12, such as a non-invasive arterial blood pressure sensor. Moreover, non-biometric sensors such as a motion sensor 26 for detecting head motion or a position sensor 28 for detecting patient body position may be included in the sensor member 12 or neck collar 14 or electronics module 16. In some embodiments, the motion sensor 26 includes one or more accelerometers, such as three accelerometers arranged to detect motion in three orthogonal directions. Small accelerometer-based motion sensors or gyro-based patient position sensors suitable for inclusion in the sensor member 12 are readily manufactured, for example using microelectronic machining (MEMS) techniques. The remote sensor member 12 in some embodiments is an ear-based sensor member that is sized and sufficiently small to fit fully within the ear canal.

To make the remote sensor member 12 lightweight, most components for operating the remote sensor member 12 are disposed in the neck collar 14. For example, an electrical power source 30, in the illustrated embodiment being two batteries, is disposed in the neck collar 14. The electrical power source 30 electrically powers components of the neck collar 14 and additionally electrically powers the biometric sensors 20, 22, 24, 25, motion sensor 26, patient position sensor 28, and optionally other components of the sensor member 12. A power pathway 32 of the flexible tether 18 conveys electrical power from the electrical power source 30 of the neck collar 14 to the sensor member 12. Because a battery, batteries, or other electrical power sources tend to be relatively heavy and bulky, disposing the electrical power source 30 on or in the neck collar 14 so that the electrical power source can be omitted from the remote sensor member 12 enables substantial reduction in size and weight of the remote sensor member 12. However, it is also contemplated to provide an electrical power source on the remote sensor member.

In similar fashion, sensor signals from the biometric sensors 20, 22, 24, 25 and from the motion sensor 26 or the patient position sensor 28 are conveyed from the remote sensor member 12 to the neck collar 14 by a data communication pathway 34 of the flexible tether 18. In the illustrated embodiment, the sensor data is conveyed as analog sensor signals which are converted to digital signal samples by a sensor signals analog-to-digital (A/D) converters 36. Disposing the A/D converters 36 on or in the neck collar 14 rather than on or in the remote sensor member 12 again reduces weight and bulk of the remote sensor member 12; however, it is contemplated to dispose A/D converters on or in the remote sensor member so as to enable the remote sensor member to directly output digital sensor signal samples.

The neck collar 14 provides a platform for disposing various types of electronics for the biometric sensor 10. For example, a digital processor 40, such as a microprocessor, microcontroller, or so forth, configured to perform executable instructions (such as software or firmware) stored in an executable memory 42 such as a read-only memory (ROM), programmable read-only memory (PROM), FLASH memory, or so forth can be included to perform various data processing tasks. For example, the digital processor 30 can be used in conjunction with a system clock 44 to time-stamp the digital sensor signal samples output by the A/D converters 36. In other embodiments, a time-stamping algorithm is integrated into the A/D converters so that they directly output time-stamped digital sensor signal samples. The time-stamped digital samples can be stored in a data storage 46, such as an electrostatic memory, FLASH memory, random-access memory (RAM), or so forth to provide trending data for the monitored biometric parameters.

The stored time-stamped digital sensor signal samples can be off-loaded to a hospital computer or other device using a wireless transceiver 48 employing a wireless electromagnetic, infrared, or other wireless communication channel. Alternatively; the neck collar 14 can include a suitable port built into the electronics module 16, such as a USB port (not shown), to enable a hospital computer or other device to temporarily connect with the neck collar 14 to off-load the stored time-stamped digital sensor signal samples. Such a wired or wireless connection 48 can also optionally be used for communicating data to the biometric monitor 10, such as for remotely silencing an alarm, or for remotely changing alarm limits, or for receiving a firmware update, or for receiving configuration information for configuring the biometric monitor 10 respective to a patient. Such configuration information may include, for example, patient identification information (e.g., name, primary physician, insurance information, or so forth), patient weight, or so forth. Configuration information may also include functional parameters, such as a selection of which of the biometric sensors 20, 22, 24, 25 should be performing active monitoring. The configuration information may be stored in the data storage 46 or in a separate storage (not shown). Depending upon the purpose served, the wireless transceiver 48 may be replaced by a transmit-only unit (e.g., if the only application is off-loading trending data) or by a receive-only unit (e.g., if the only application is receiving alarm limits or alarm silence commands, or receiving patient or configuration data).

Typically, it is desirable to have a real-time output, in addition to or instead of the stored trending data that is later off-loaded. In the illustrated embodiment, a display 50, such as an LED or LCD display, shows the blood oxygen saturation (currently showing at 98.3% in FIG. 1) and the heart rate (currently showing at 84 bpm). The heart rate is readily derived from the sensor signal of the $SpO_2$ sensor 20 using a known heart rate derivation algorithm performed by the digital processor 40. The display 50 is arranged on the electronics module 16 so that it is readable when the neck collar 14 is worn by a patient. This allows for the complete patient monitor to always be with an ambulating patient. The illustrated embodiment also includes an audio alarm 52, and the digital processor 40 is configured to activate the audio alarm 52 responsive to a biometric sensor signal or signals corresponding to a vital sign or vital signs satisfying an alarm criterion. For example, if the blood oxygen saturation drops below a threshold value such as 90%, the alarm may be configured to activate, or if the heart rate exceeds a threshold value such as 150 bpm the alarm may be configured to activate. Should both of these above stated conditions occur simultaneously, a more serious alarm may be configured to activate. Instead of or in addition to the audio alarm 52, the digital processor 40 may be configured to cause the wireless transceiver 48 to output a suitable warning signal that is detectable and interpretable by wireless receivers disposed throughout the hospital.

The illustrated example biometric monitor 10 includes numerous features, such as the visual display 50, audio alarm 52, components 46, 48 for storing and off-loading trending biometric data, and so forth. The inclusion of these numerous features is enabled by using the neck collar 14 to support most components implementing these features, so that the remote sensor member 12 can remain lightweight. Thus, the advantages of having an in-ear sensor member (such advantages including, for example, core body, versus skin, temperature monitoring, reduced ambient light interference, reduced motion artifacts compared with sensor members disposed on the arm, or hand, or finger, and so forth) are retained without commensurate limitations on the size or bulkiness of components driving the biometric sensors or processing sensor data. The ear sensor member can be an in-ear sensor member, or can mount over-the-ear, or can clip onto the ear lobe, or so forth. For $SpO_2$ measurements, an ear lobe clip arrangement can be convenient and effective for acquiring accurate $SpO_2$ measurements. The in-ear arrangement is especially good for core body temperature and SpO2 measurements. It is contemplated for the in-ear sensor member to include two or more vital sign parameters, such as $SpO_2$ and core body temperature. The flexible tether 18 optionally also includes an earlobe clip 56 or other feature for securing the tether 18 to the earlobe to reduce motion artifacts caused by head movement and reduce the likelihood that head movement may dislodge the ear sensor member 12.

Without the tether, it is difficult to convey electrical power from the neck collar to the remote sensor member, although the use of wireless power-carrying electromagnetic power transmissions is contemplated. In some embodiments the remote sensor member may be adequately powered by a small on-board electrical power source, such as a battery or batteries commonly used in in-the-ear style hearing aids. In such embodiments, such as an active electrocardiographic electrode or electrodes, it is contemplated to employ a wireless low power communication link operatively connecting the remote sensor member and the electronics of the neck collar. Some suitable wireless low power communication links may employ a Bluetooth protocol, a body-coupled communication protocol, or so forth. The on-board power source of the remote sensor member should then produce sufficient power to drive both the biometric sensor or biometric sensors and the on-board transmitter that conveys the sensor data to the neck collar. Such an arrangement retains the benefit of placing the electronics and output and/or tending/off-loading elements on the neck collar, thus substantially reducing the size and weight of the remote sensor member.

In some embodiments, only some of the outputs 48, 50, 52 are provided. For example, the biometric monitor may include only a visual display. If the trending aspect is omitted, then time-stamping of digital sensor signal samples is also optionally omitted. Those skilled in the art may also choose to incorporate other features which take advantage of the flexibility provided by the neck collar-based electronics. In some embodiments, the neck collar display 50 may include additional textual data, for example patient information and/or special instructions for patient care. The neck collar 14 can also include some of the biometric sensors, such as example neck collar based sensors 53, rather than placing all sensors on the remote sensor member 12. The additional neck collar based sensors 53 may include, for example, electrocardiographic electrodes, a sudden infant death syndrome (SIDS) detector, a reflective $SpO_2$ sensor, a body temperature sensor, non-invasive pulse/pressure sensors, or so forth. A temperature sensor can be included in the neck collar so that the electronics are operational only when the temperature corresponds to body temperature (thus indicating that the collar is actually being worn by a patient). It is also contemplated to include a hearing aid in the remote sensor member, with power for driving the hearing aid supplied by the neck collar via the power pathway 32. Speakers can also be provided for converting remote electronic communications, such as music or instructions, into sound. In some embodiments, it is contemplated for the remote sensor member 12 to be detachable from the flexible tether 18, or detachable from the neck collar 14, and to be disposable. In such embodiments, each patient receives a new disposable sensor member. In some embodiments it is also contemplated for the neck collar 14 to be detachable from the electronics 16 and to be disposable. In such embodiments, each patient receives a reusable electronics attached to a disposable neck collar.

In another contemplated option, a light emitting device, such as a light emitting diode (LED) 54 is provided and configured to flash at a frequency corresponding with the heart rate derived from the signal acquired from the $SpO_2$ sensor 20. The corresponding flash rate can be equal to the heart rate (e.g., a heart rate of 80 bps producing 80 flashes per minute) or can be a fraction of the heart rate (e.g., the LED 54 may flash once for every five heart beats). While the illustrated biometric monitor 10 is intended for medical monitoring, it is also contemplated to design the biometric monitor 10 as a fashion accessory. For such an application, it is contemplated to have the flashing LED as the principal output. In such an application, the LED may be large, especially bright, or may comprise an array of LEDs, or may be configured to have different LEDs light at different heart rates (for example, flashing yellow LEDs at normal heart rates and red LEDs at elevated heart rates to indicate increased excitement). Such fashion devices are expected to be suitable for use in dance clubs or other fashionable settings, or for general wear at work, school, or recreation.

The LED 54 can be located instead or additionally on the remote ear-based sensor member 12. In some embodiments, the remote sensor member includes vital signs sensors such as pulse rate, $SpO_2$, blood pressure, or so forth, along with a battery or other power supply, and a digital processor for processing data from the sensors and for flashing or otherwise controlling one or more LEDs disposed on the ear-mounted sensor member. For example, the processor may cause the LED to flash or blink in correspondence with the heart rate, or to light or change color as one or more vital signs crosses a danger threshold. Such a device may be useful, for example, in triaging injured persons in a disaster situation.

FIG. 1 shows in phantom an optional second remote ear-based sensor member 12' connected with the flexible tether 18 by a "Y" split. The optional second ear sensor member 12' can be used in conjunction with the ear sensor member 12 to provide both left and right ear sensor members 12, 12'. This arrangement can be used to provide redundancy in case a sensor in one of the ear sensor members fails. Additionally or alternatively, providing left and right ear sensor members can increase patient comfort by providing symmetry. In some embodiments, the left and right ear sensor members 12, 12' are used in conjunction with processing performed by the digital processor 40 to generate a differential signal based on left and right signals received from left and right biometric sensors disposed in the left and right ear sensor members 12, 12', respectively. Such a differential signal can be useful in electrocardiographic measurements, arterial blood pressure measurements, and so forth. Alternatively to the "Y" split, the tether can include two separate tethers so that the second ear sensor member 12' can be attached directly to the collar 64 or electronics box 16 at a separate location.

Tests of various neck collars for use in the biometric monitor have shown that design of the neck collar can substantially impact patient comfort and mobility. It has been found that providing an open front portion 60 is advantageous both in terms of ease of application and patient comfort and to provide a gap for oxygen tubes and so forth. It has been found that a relatively large opening 60 is suitable. For example, having the neck collar 14 extend greater than 180° and less than about 200° around the neck provides sufficient retention of the neck collar 14 without pinching the front of the patient's throat. In some embodiments, the neck collar 14 extends greater than about 90° and less than about 330° around the neck, or more preferably about 135° and less than about 270° around the neck, or most preferably about 180° and less than about 200° around the neck. Additionally, it has been found that suppressing rotation of the neck collar 14 around the neck is advantageous to promoting patient comfort. Toward this end, the neck collar 14 includes a central metal portion 62 and polymer-coated, e.g., PlatSil®-coated end portions 64, 66 that cling to the neck to suppress rotation. Additionally, providing an adjustable collar size is advantageous to promoting comfort. Toward this end, the neck collar 14 includes a post-and-holes system with holes 68 for adjusting the position of connection of the PlatSil® polymer-coated end portions 64, 66 to the central metal portion 62.

Figure 3:
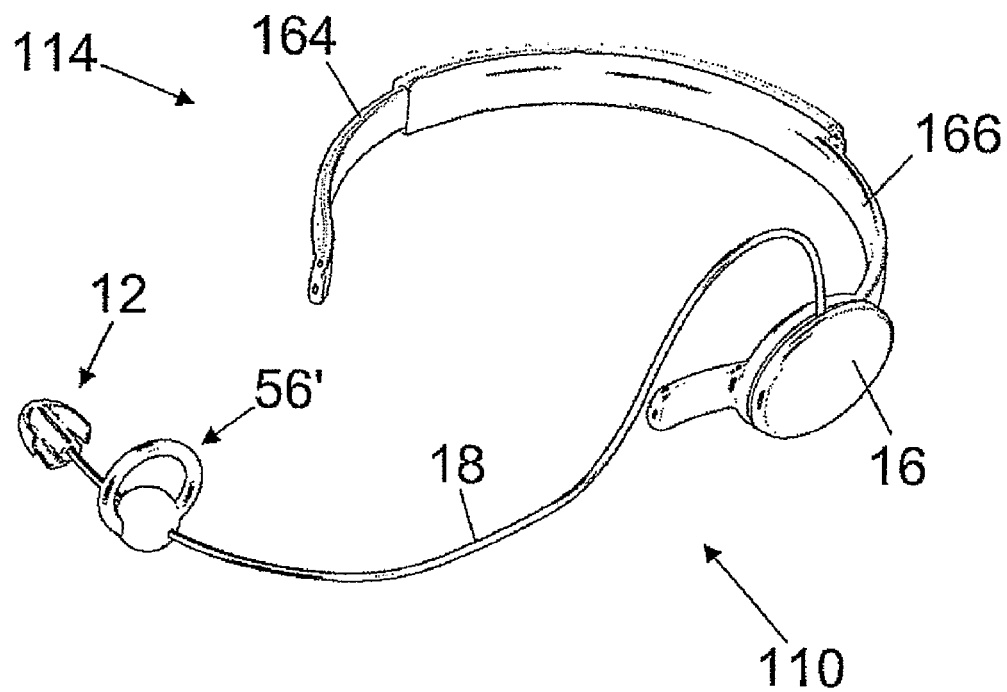
FIG. 3 shows a perspective view of a biometric monitor including an in-ear biometric sensor member tethered with electronics disposed on and/or in a neck collar that has a continuously adjustable collar size.

With reference to FIGS. 3-9, other neck collar designs have been found to enhance patient comfort. FIG. 3 shows a biometric monitor 110 with a neck collar 114 that includes slidably adjustable portions 164, 166 to provide a continuous collar size adjustment. The biometric monitor 110 also includes a mechanical stopper 56' in place of the earlobe clip 56 of the biometric monitor 10 of FIG. 1 to stabilize the flexible tether 18 and preclude accidental over-insertion of the ear-based remote sensor member 12 into the ear canal.

Figure 4:
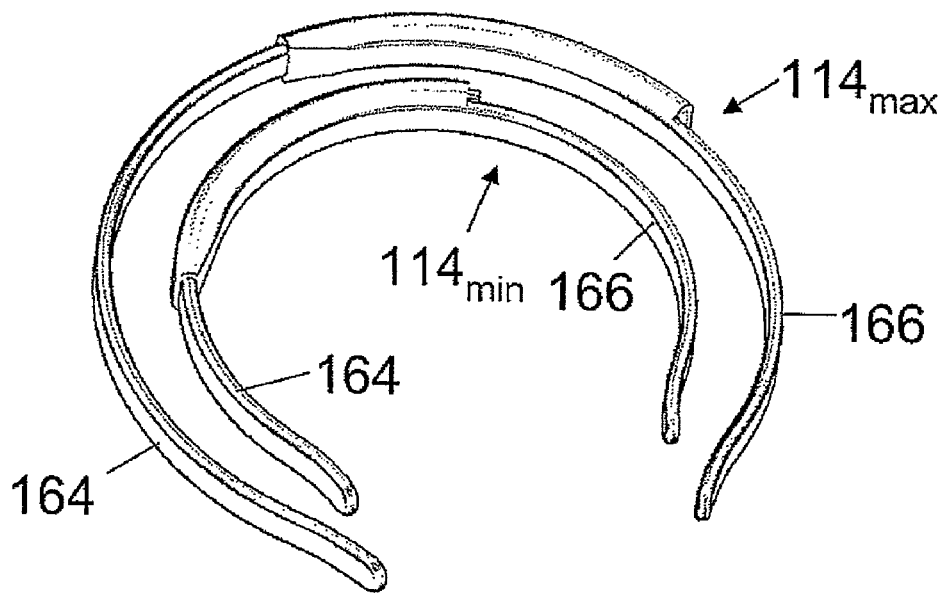
FIG. 4 shows perspective views of a continuously adjustable neck collar of the biometric monitor of FIG. 3 adjusted to the maximum and minimum collar sizes.

FIG. 4 shows a minimum collar size arrangement $114_{min}$ and a maximum collar size arrangement $114_{max}$ of the neck collar 114.

Figure 5:
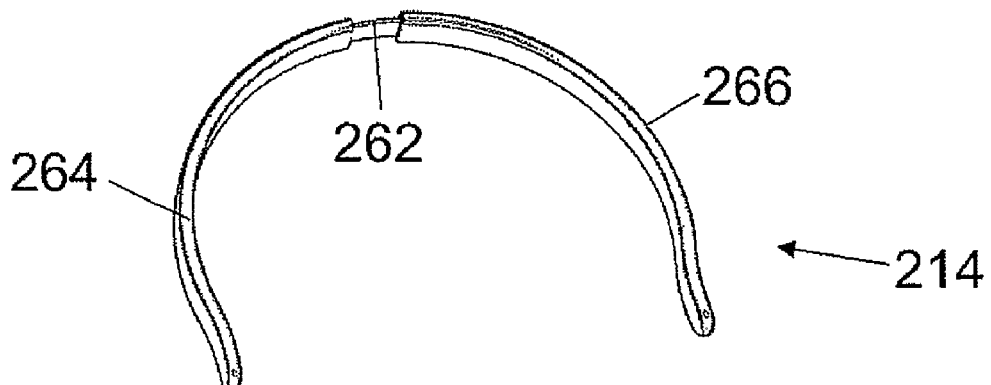
FIG. 5 shows a perspective view of an alternative neck collar having a continuously adjustable collar size that is symmetrical, adjusted to the minimum neck size.
Figure 6:
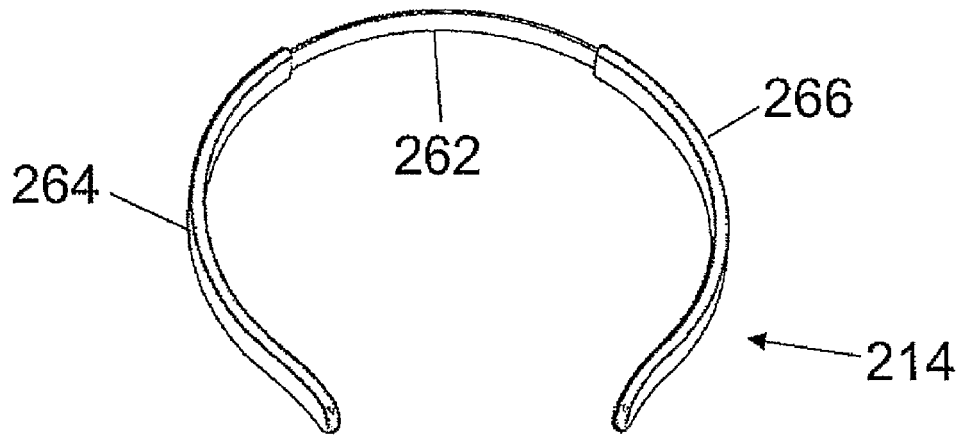
FIG. 6 shows a perspective view of the adjustable neck collar of FIG. 5 adjusted to the maximum neck size.
Figure 7:
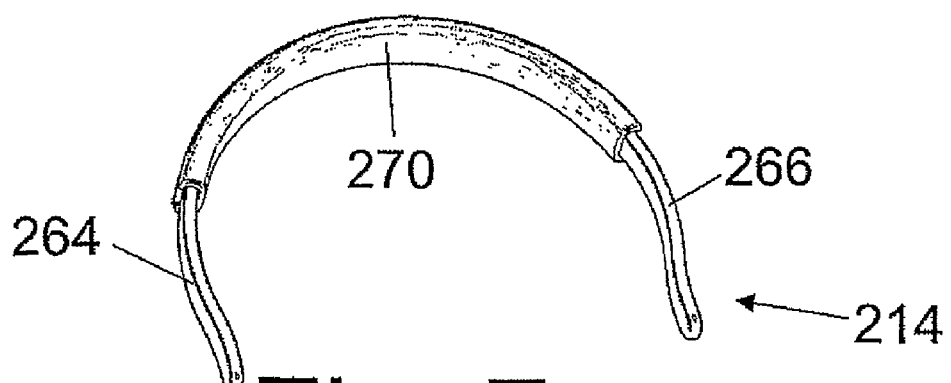
FIG. 7 shows a perspective view of the adjustable neck collar of FIG. 5 with a cover for the region of the neck collar that is exposed by the sliding collar size adjustment.

FIGS. 5-7 show another suitable neck collar 214 that is similar to the neck collar 14 except that the discrete post-and-holes collar size adjustment is replaced by a sliding adjustment in which polymer-coated end portions 264, 266 slidably adjust on a central metal portion 262. FIG. 5 shows the neck collar 214 adjusted to minimum collar size, while FIG. 6 shows the neck collar 214 adjusted to maximum collar size. FIG. 7 shows the neck collar 214 further including an optional cover 270 for covering the portion of the central metal region 262 of the neck collar 214 that is exposed by the sliding collar size adjustment. The cover 270 can enhance patient comfort, and optionally has a high-friction surface to further inhibit neck collar rotation.

Figure 8:
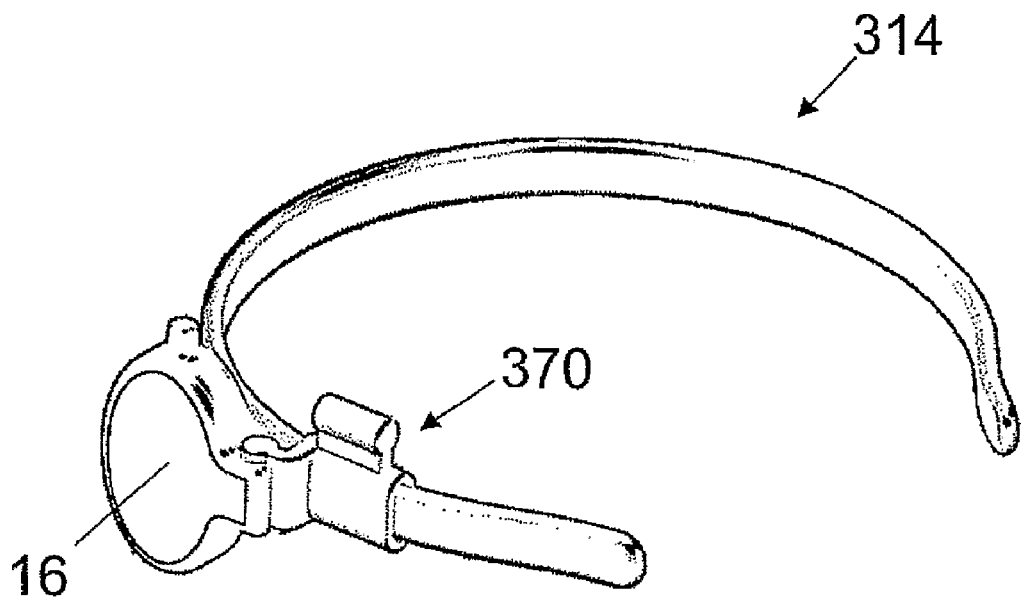
FIG. 8 shows a perspective view of an alternative neck collar in which the collar size is fixed but the position of an electronics module on the collar is adjustable.

FIG. 8 shows another suitable neck collar 314, which does not have an adjustable collar size, but which does include a slidable bracket 370 for slidably positioning and/or detaching the electronics module 16 anywhere along the collar 314. It is also contemplated to include both an adjustable collar size and a slidably movable and/or detachable electronics module. Moreover, although not illustrated it is contemplated to dispose the electronics on a flexible circuit board that is integrated into the neck collar, so that the separate electronics module 16 can be omitted. The electrical power source in such arrangements can be either a set of small batteries or a thin-film flexible battery. Such a distributed arrangement is expected to further enhance patient comfort.

Figure 9:
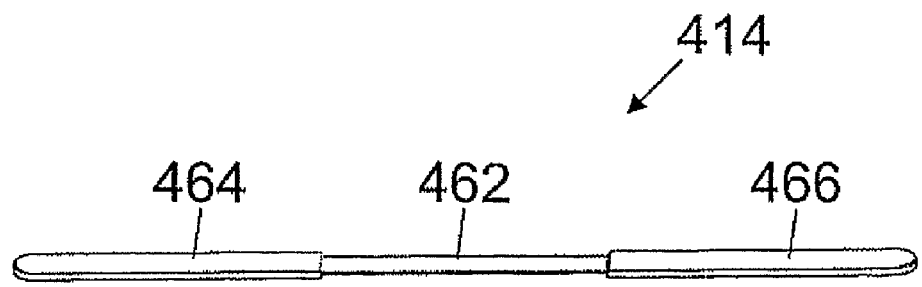
FIG. 9 shows a perspective view of an alternative neck collar that is deformable to fit the patient's neck.

FIG. 9 shows another suitable neck collar 414 which includes a central metal portion 462 and polymer-coated end portions 464, 466 that cling to the neck to suppress rotation. In this embodiment the central metal portion 462 is deformable to fit the patient's neck. The electronics module 16 is suitably attached by the slidable bracket 370 of FIG. 8, or by a fixed bracket. The central metal portion 462 acts as a custom-bendable stiffener to enable the neck collar 414 to be deformed to comport with any of the illustrated embodiments or other related embodiments.

With returning reference to FIG. 1, in addition to patient comfort, it is advantageous to take measures to ensure that the biometric data are accurate. It has been found that certain measurements, such as the heart rate derived from the sensor signal of the $SpO_2$ 20, are sensitive to head movement. Including the motion sensor 26 provides a mechanism for accounting for such motion-related error.

With reference to FIG. 10, a suitable method implemented by the digital processor 40 is described, which makes accounts for error in the heart rate derived from the sensor signal of the $SpO_2$ sensor 20 caused by head movement sensed by the motion sensor 26. A heart rate calculator algorithm 500 is performed to derive the heart rate from the $SpO_2$ sensor signal. Based on the signal produced by the motion sensor 26, a decision block 502 determines whether the derived heart rate is reliable. For example, the derived heart rate may be deemed reliable if the absolute detected motion is less than a threshold value, and may be deemed unreliable if the absolute detected motion exceeds the threshold value. Alternatively, the motion sensor signal may be used only when the derived SpO2 sensor signal quality is below a given threshold. If the derived heart rate is deemed to be reliable, then the newly derived heart rate reading is stored 504 in the data storage 46; otherwise, it is not stored. The display 50 then displays 506 the last stored heart rate reading. Since the storing operation 504 stores only reliable heart rate readings, this displaying 506 displays only reliable heart rate readings, albeit possibly with some time lag involved if the most recent heart rate reading was deemed to be unreliable. Rather than discarding unreliable heart rate readings, it is also contemplated to perform a correction of unreliable heart rate readings, for example using suitable filtering and utilizing signal quality measurements. Additionally, it is contemplated that the unreliable data will be stored and have value during product development and in research applications. With continuing reference to FIG. 10, signals obtained from the motion sensor 26 may also be utilized by decision block 503 to detect that a patient has fallen and call a fallen patient alarm 510.

With reference to FIG. 11, signals obtained from the motion sensor 26 and position sensor 28 may be utilized to determine the position and ambulating activity (if any) of the patient. In example FIG. 11, the output of the position sensor 28 is used by a decision block 602 to determine whether the patient is sitting or standing. If the patient is sitting or standing, then an ambulating activity decision block 604 processes the output of the motion sensor 26 to determine whether the patient is walking 606 or sitting 608. Such ambulating activity, or lack thereof, is suitably logged into the data storage 46 by an activity logger 610. On the other hand, if the decision block 602 determines that the patient is neither standing nor sitting, then the patient's position is optionally more precisely determined. For example, high-Fowler, raid-Fowler, low-Fowler, supine, and Trendelenberg decision blocks 612, 614, 616, 618, 620, respectively, suitably determine whether the patient is in the high-Fowler position 622, mid-Fowler position 624, low-Fowler position 626, supine position 628, or Trendelenberg position 630, respectively. A position logger 632 suitably logs the position of the patient into the data storage 46. The ambulating activity and position logging provides valuable feedback about patient positions and physical activity to the care providers. This information is optionally used to assist with correlating specific physiological alarms with patient activity as well as to determine the well-being of the patient and assessing discharge possibilities. The body position signal information is optionally also utilized by a parameter correction 634 to automatically correct parameter calculations. For example, the noninvasive arterial blood pressure parameter can automatically correct itself by knowing whether the patient is sitting upright, sitting in one of the Fowler positions, or is lying in a supine position.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A biometric monitor comprising:
an ear sensor member configured to be mounted within a patient's ear canal and including one or more biometric sensors configured for operative coupling with the patient, the ear sensor member not including an electrical power source;
a neck collar including an electrical power source disposed on or in the neck collar and electronics for operating the ear sensor member, the ear sensor member being separate from and not disposed on the neck collar; and
a flexible tether connecting the ear sensor member and the neck collar, the flexible tether including (i) a data communication pathway conveying sensor data from the one or more biometric sensors of the ear sensor member to the electronics of the neck collar and (ii) a power pathway conveying electrical power from the electrical power source of the neck collar to the ear sensor member to electrically power at least one biometric sensor of the ear sensor member.

2. A biometric monitor comprising:
an ear sensor member configured to be mounted within a patient's ear canal, the ear sensor member including at least a motion sensor configured to sense head movement and an SpO$_2$ sensor;
a neck collar including electronics for operating the ear sensor member, the ear sensor member being separate from and not disposed on the neck collar; and
a tether connecting the ear sensor member and the neck collar;
wherein the electronics of the neck collar are configured to derive a heart rate from a signal acquired from the SpO$_2$ sensor including correcting the heart rate for head movement sensed by the motion sensor.

3. The biometric monitor as set forth in claim 2, wherein the motion sensor includes one or more accelerometers.

4. The biometric monitor as set forth in claim 2, wherein the motion sensor and electronics is capable of detecting that the patient has fallen and annunciates a fallen patient alarm.

5. The biometric monitor as set forth in claim 1, wherein the ear sensor member or the neck collar includes at least a body position sensor and electronics that is capable of detecting that the patient is sitting/standing upright, sitting in a Fowler position, or lying in a supine position.

6. The biometric monitor as set forth in claim 5, wherein the position sensor, and electronics is capable of determining body position and utilizing the determined body position to automatically correct a biometric parameter for body position.

7. The biometric monitor as set forth in claim 5, wherein the motion sensor, the position sensor, and electronics are configured to detect and log patient activity and body position.

8. The biometric monitor as set forth in claim 1, wherein the sensor data is conveyed along the flexible tether as one or more analog electrical sensor signals, and the electronics of the neck collar include:
one or more analog-to-digital converters that receive the one or more analog electrical sensor signals and convert said one or more analog electrical sensor signals to digital electrical sensor signal samples.

9. The biometric monitor as set forth in claim 1, wherein the electronics of the neck collar include:
a data storage storing sensor signals received from the one or more biometric sensors as time-stamped sample values; and
a wireless receiver, transmitter, or transceiver configured to perform at least one of (i) off-loading content of the data storage from the biometric monitor and (ii) receiving configuration information for configuring the biometric monitor.

10. The biometric monitor as set forth in claim 1, wherein the neck collar further includes at least one of:
an alarm, the electronics of the neck collar being configured to activate the alarm responsive to a signal or signals from one or more of the biometric sensors satisfying an alarm criterion; and
a display arranged on the neck collar to be readable with the neck collar installed on a neck, the electronics being configured to operate the display based on at least one sensor signal acquired from the one or more biometric sensors.

11. The biometric monitor as set forth in claim 1, wherein the electronics are one of (i) disposed in an electronics module attached to the neck collar and (ii) disposed on a flexible circuit board integrated into the neck collar.

12. The biometric monitor as set forth in claim 1, wherein the neck collar is open in a front portion.

13. A biometric monitor comprising:
   at least one remote sensor member including one or more biometric sensors configured for operative coupling with a patient;
   a neck collar including electronics for operating with the remote sensor member, the remote sensor member being separate from and not disposed on the neck collar, wherein the neck collar extends greater than about 90° and less than about 330° around the neck; and
   a communication link operatively connecting the remote sensor member and the electronics of the neck collar.

14. The biometric monitor as set forth in claim 1, wherein the flexible tether includes one of: unshielded single or multi-conductor wire, shielded single or multi-conductor wire, wireless electromagnetic transmissions, one or more fiber optics.

15. The biometric monitor as set forth in claim 13, wherein the neck collar extends greater than about 135° and less than about 270° around the neck.

16. The biometric monitor as set forth in claim 13, wherein the neck collar extends greater than about 180° and less than about 220° around the neck.

17. The biometric monitor as set forth in claim 13, wherein the neck collar is open in a front portion.

18. The biometric monitor as set forth in claim 1, wherein the one or more biometric sensors measure heart rate, the neck collar includes a light emitter, and the electronics of the neck collar control the light emitter to blink at a frequency corresponding with the heart rate.

* * * * *